United States Patent [19]

Wang et al.

[11] Patent Number: 5,080,765
[45] Date of Patent: Jan. 14, 1992

[54] METHOD FOR DETERMINING IDENTIFICATION AND CONCENTRATION OF AN ATMOSPHERIC COMPONENT

[75] Inventors: Da Y. Wang, Lexington; Daniel T. Kennedy, Burlington, both of Mass.; Burton W. MacAllister, Hudson, N.H.

[73] Assignee: GTE Laboratories Incorporated, Waltham, Mass.

[21] Appl. No.: 453,566

[22] Filed: Dec. 20, 1989

[51] Int. Cl.$^5$ .......................................... G01N 27/406
[52] U.S. Cl. .............................. 204/153.1; 204/153.2; 204/153.18; 204/425; 204/426
[58] Field of Search ............. 204/153.1, 153.18, 153.2, 204/421–429

[56] References Cited

U.S. PATENT DOCUMENTS

| | | | |
|---|---|---|---|
| 2,773,237 | 12/1956 | Offutt et al. | 204/153.1 |
| 4,450,065 | 5/1984 | Yamada et al. | 204/426 |
| 4,722,779 | 2/1988 | Yamada et al. | 204/426 |
| 4,770,760 | 9/1988 | Noda et al. | 204/425 |
| 4,909,072 | 3/1990 | Logothetis et al. | 204/426 |

FOREIGN PATENT DOCUMENTS 1545737 5/1979 United Kingdom .
1584991 2/1981 United Kingdom .

OTHER PUBLICATIONS

Soviet Inventions Illustrated, El Section, Week 8720, Jul. 1, 1987.
Soviet Inventions Illustrated, El Section, Week 8343, Dec. 7, 1983.
Su-Il Pyun, Y-E. Ihm, "Electrical conduction of partially stabilized zirconia $Zr_{0.94}Ca_{0.06}O_{1.94}$ as a function of temperature and oxygen partial pressure" J. of Mat. Sci. 17 2577–2584 (1982).

Primary Examiner—T. Tung
Attorney, Agent, or Firm—Carl F. Ruoff

[57] ABSTRACT

Apparatus and method for determining the identity and concentration of one or more components in a test atmosphere having a known concentration of oxygen. A solid electrolyte oxygen sensor is used, having a first solid electrolyte wall in contact with, and interposed between, a first electrode and a second electrode and a second solid electrolyte wall in contact with, and interposed between a third electrode and a fourth electrode. The second and fourth electrodes are in communication with the test atmosphere. A partition wall separates the first and third electrodes forming a first chamber bounded by the first wall and the partition wall and a second chamber bounded by the partition wall and the second wall. Diffusion limiting means inhibit gas-flow of the gas from the test atmosphere to the first chamber and from the first chamber to the second chamber. A first negative voltage (or positive voltage when the unknown component has a concentraion larger than that of a stoichiometric gas mixture) is applied to the first and second electrodes generating a first electrical current on a first electric current plateau. Simultaneously the EMF across the third and fourth electrodes is measured. These two numbers are correlated with a table to determine gas component identity and concentration. Alternatively a first negative voltage is applied to the first and second electrodes generating a first electrical current. Simultaneously a second negative voltage is applied to the third and fourth electrodes generating a second electrical current. The magnitudes of said first and second voltages are in contrast to each other (the first voltages is low and the second voltage is high or vise verse, with their difference kept at least 100 mV). The second current is measured and is correlated with a figure to determine gas concentration or hydrogen-equivalent gas concentration.

6 Claims, 11 Drawing Sheets

EMF LEVEL AND POLARITY (mV)
(SECOND PAIR OF ELECTRODES)

| +920 | −220 | LIMITING CURRENT LEVEL (mA) (FIRST PAIR OF ELECTRODES) |
|---|---|---|
|  | HYDROGEN 15% | 0.025 |
|  | HYDROGEN 17% | 0.11 |
| METHANE 12.6% | HYDROGEN 17.7% | 0.15 |
|  | HYDROGEN 19% | 0.20 |
|  | HYDROGEN 21% | 0.29 |
|  | HYDROGEN 23% | 0.38 |

METHOD FOR DETERMINING IDENTIFICATION AND CONCENTRATION OF AN ATMOSPHERIC COMPONENT

INCORPORATION BY REFERENCE

U.S. patent application Ser. No. 07/198,028 filed May 24, 1988 by Wang, MacAllister, and Kennedy for Gas Sensing Apparatus, assigned to the same assignee as this now U.S. Pat. No. 4,897,174, is hereby incorporated by reference.

BACKGROUND OF THE INVENTION

This invention pertains to measurements of atmospheric components, and more particularly is concerned with such measurements using solid electrolyte sensors.

Solid electrolyte sensors are used extensively to monitor exhaust gases from engines and other combustion processes to determine the percentage of oxygen in the test atmosphere. From this measurement the efficiency of the combustion process can be determined. Reactive gases and water vapor can affect the accuracy of the oxygen reading. What has not been recognized until this invention is that this phenomenon, which is generally considered detrimental to measurements, can be utilized for determining the identity and concentration of a component in a test atmosphere having a known concentration of oxygen.

An object of the invention is to provide a method for determining the identity and concentration of a component in a test atmosphere having a known concentration of oxygen using a solid electrolyte sensor.

Another object of the invention is to provide a solid electrolyte oxygen sensor for determining the identity and concentration of a component in a test atmosphere having a known concentration of oxygen.

SUMMARY OF THE INVENTION

Briefly, according to one aspect of the invention, there is provided means for determining the identity and concentration of a component in a test atmosphere having a known concentration of oxygen. One solid electrolyte oxygen sensor is used which has a first solid electrolyte wall in contact with and interposed between a first and a second electrode and has a second solid electrolyte wall in contact with and interposed between a third and a fourth electrode. There is a partition wall that is between the first and second electrolyte wall. A first gas chamber is formed between the partition wall and the first electrolyte wall. The partition wall and the second electrolyte wall forms a second gas chamber. A first gas aperture allows the testing gas to pass from the ambient atmosphere into the first gas chamber, and a second gas aperture on the partition wall allows gas to pass between the first and the second gas chambers. The first electrode is exposed to the gas inside the first gas chamber and the third electrode is exposed to the gas inside the second gas chamber. The second and fourth electrodes are exposed to the ambient testing gas.

A first negative voltage is applied across the first and second electrodes causing electrochemical pumping of oxygen and a first electric current to flow through the first electrolyte wall. Simultaneously an electromotive force (Nernst voltage) is measured between the third and fourth electrodes. The first negative voltage has a magnitude to cause the first electric current to be on a first current plateau. The magnitude of the first electric current is measured.

A table correlating pairs of numbers representing various combinations of the first current magnitude and the emf (Nernst voltage) values with the corresponding identity and concentration of one or more components is provided. The measured first magnitude of electric current and the magnitude of the emf are matched with the pairs of numbers in the table and the corresponding identity and concentration of one or more components are determined.

Another aspect of the present invention is to provide the identity and concentration of a reducing component in a gas mixture having a known oxygen concentration such as air in which the ratio between the reducing component and the oxygen exceeds the stoichiometric number of the mixture. In this case, a first positive voltage is applied across the first and the second electrodes. The magnitude of the first voltage is high enough to produce a first limiting electric current but not high enough to exceed this saturation-current condition. The magnitude of the electric current is measured. Simultaneously an electro-motive force (Nernst voltage) is measured between the third and fourth electrodes.

A table correlating pairs of numbers representing various combinations of the first current plateaus and the emf values with the corresponding identity and concentration one or more components is provided. The measured plateau of the first electric current and the magnitude of the emf are matched with pairs of the numbers in the table and the corresponding identity and concentration one or more components are determined.

In another aspect of the present invention, the concentration, or the hydrogen-equivalent concentration of a reducing gas in a gas mixture having a known oxygen concentration can be determined. A first negative voltage is applied across the first and second electrodes and a second negative voltage is applied across the third and fourth electrodes. The second voltage produces a second electric current and its magnitude and sign are measured.

Plots of current values versus gas concentration for various gas components are provided. The measured magnitude and sign of the second electric current are matched with the value and sign of the current in a plot and its concentration or hydrogen-equivalent concentration can be determined.

BRIEF DESCRIPTION OF THE DRAWING

FIG. 2 has four illustrations, (a) and (b) are the I-V plots for methane and hydrogen in air. There are two current plateaus over the pumping voltage range for both gases. (c) and (d) are the corresponding emf readings (Nernst voltage) taken while the first pair of electrodes are energized and pumping oxygen.

FIG. 3 (a) and (b) show the linear relationships between the low-plateau limiting current (dark circles) and the gas concentration for methane and hydrogen gas mixtures. In the same plots, the corresponding emf readings (open circles) are given.

FIG. 7 (a) shows the limiting currents for methane in air. There is one current plateau over a voltage range of 100 mV to 1100 mV, 7 (b) shows the corresponding emf readings taken while the first pair of electrodes are pumping oxygen.

FIG. 8 (a) shows the limiting currents for hydrogen in air. There is one current plateau over a voltage range of 100 mV to 1100 mV, 8 (b) shows the corresponding emf readings taken while the first pair of electrodes are pumping oxygen.

DETAILED DESCRIPTION OF THE PREFERRED EMBODIMENT

Figure 1:
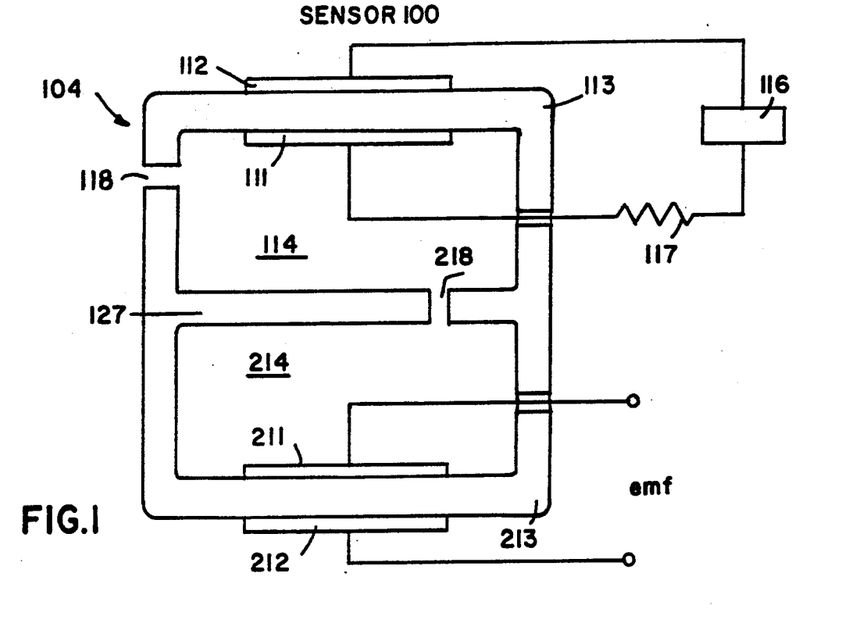
FIG. 1 illustrates in schematic form a multi-gas sensor suitable for practicing the invention.

FIG. 1 illustrates, in schematic form, an oxygen sensor 100, suitable for practicing the invention. Sensor 100 includes two pairs of electrodes 111, 112 and 211, 212, each pair is disposed on opposite sides of two solid electrolyte walls 113 and 213. Each electrode can be a layer of metal, e.g. platinum, or an electrically conducting ceramic deposited upon the surface of the solid electrolyte. The solid electrolyte can be any oxygen conducting material, preferably yttria or calcia stabilized zirconia, or similarly doped ceria. Both pairs of electrodes; 111 and 112, 211 and 212, hereinafter called the first, second, third, and fourth electrode respectively, are exposed to the gaseous medium to be tested, referred to as test atmosphere 104.

There is a partition wall 127 which separates the two pairs of electrodes. The partition wall 127 can be any material as long as its thermal-mechanical properties match those of walls 113 and 213, and its electrical resistivity is high enough so that the two pairs of electrodes are electrically insulated from each other. The preferred material is zirconia partially stabilized with yttria or calcia. The first electrolyte wall 113 and the partition wall 127 enclose the first gas chamber 114 which has a gas aperture 118 opening to the ambient gas 104. The second electrolyte wall 213 and the partition wall 127 enclose a second gas chamber 214 which has a gas aperture 218 opening to the first gas chamber 114. Other than the difference in the layout, details of the construction of one such a sensor are similar to that given by U.S. patent applications Ser. No. 07/198,028 filed May 25, 1988 by Wang, MacAllister, and Kennedy for Gas Sensing Apparatus.

To practice the method of the present invention, the test atmosphere should contain a known percentage of oxygen before mixing the gases and may be air with an unknown component such as a reactive gas or water vapor. The purpose of the method is to determine the identity and concentration of the unknown component. The whole sensor 100 is immersed in the test atmosphere. When a sufficient negative voltage is applied between the first and second electrodes 111 and 112, oxygen is pumped from atmosphere 114 through the solid electrolyte wall 113 to the gaseous medium 104. This voltage is called the pumping voltage and is provided by a voltage source 116.

In response, electric current will flow through solid electrolyte wall 113. This current is called the oxygen limiting current. This oxygen limiting current may be determined by measuring the voltage across resistor 117 in series with the pumping voltage source 116 and the sensor. In conventional oxygen sensor measurements, the current is a function of the concentration of oxygen in the test atmosphere.

The physical barrier 118, which is a small aperture or a gas permeable membrane is provided between the surface of electrode 111 and test atmosphere 104 for limiting the flow of gas from the test atmosphere 104 to the first electrode 111 in such a way that for a wide range of pumping voltage the oxygen current is at its limiting level, i.e., nearly constant as the pumping voltage is varied over a wide range.

Likewise, a physical barrier 218 which can be a small aperture or a gas permeable membrane is provided to separate the gas in chamber 214 from the gas in chamber 114. The barrier 218 limits flow of the gases between the cells and is necessary for accurate readings.

Figure 2A:
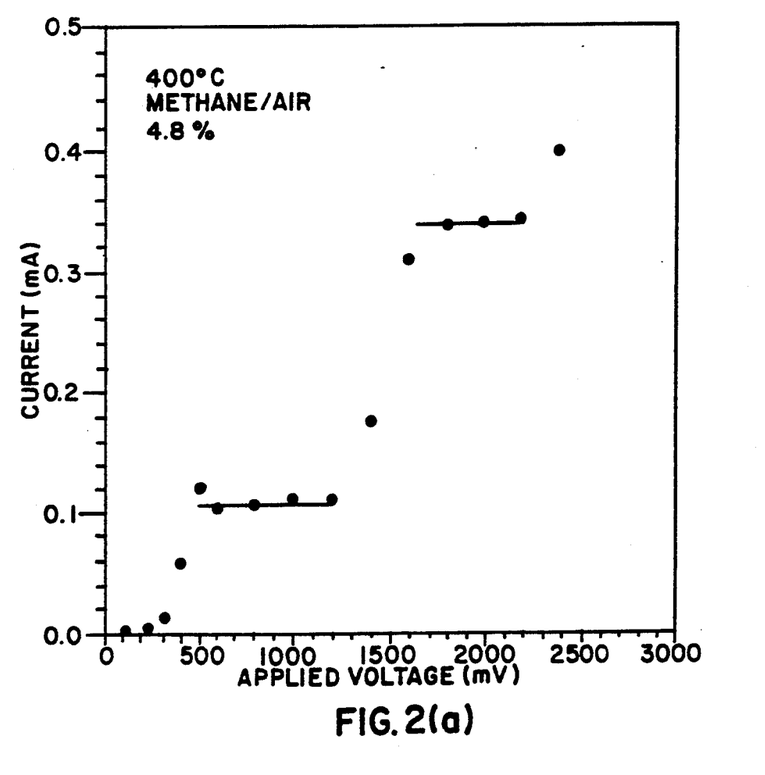
Figure 2B:
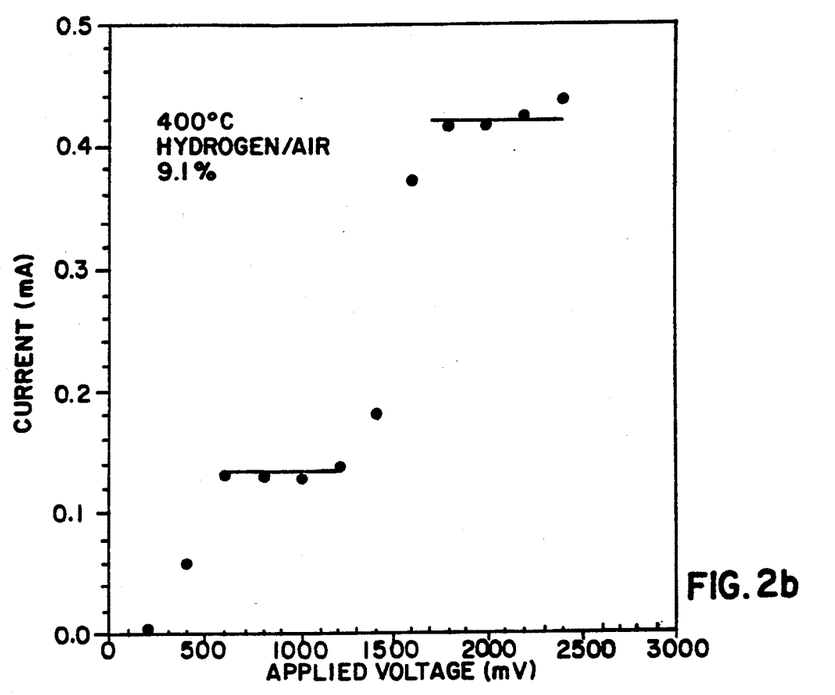

The phenomenon of current plateaus is illustrated by the curve in FIGS. 2(a) and (b) where two plateaus occur for a methane/air gas mixture and a hydrogen/air gas mixture. For both cases, the first limiting current occurs for a pumping voltage between 400 mV and 1300 mV. The second limiting current occurs at a pumping voltage between approximately 1800 mV to 2500 mV.

An important property of such an oxygen sensor is that in the presence of a reactive gas or fully oxidized gas such as water vapor in the test atmosphere, the electric current flowing through the solid electrolyte wall is approximately constant for two ranges of pumping voltages if all other parameters such as test atmospheric component concentration and temperature of the sensor remain constant. For each of the two ranges that the current is approximately constant, the current is said to be on a current limiting plateau.

The lower of the two plateaus occurs because at lower pumping voltages, the presence of a reactive gas or water vapor in the test atmosphere will lower the amount of oxygen electrochemically pumped through the solid electrolyte wall, and therefore limit the corresponding electric current. The higher the concentration of reactive gas or water vapor in the test atmosphere, the lower will be the limiting current plateau. The reason is that, in the case of a reactive gas, at lower pumping voltages the gas catalytically reacts with oxygen at the electrode. In the case of fully oxidized gas, the oxygen concentration of the test gas is diluted by the oxidized gas.

Figure 3A:
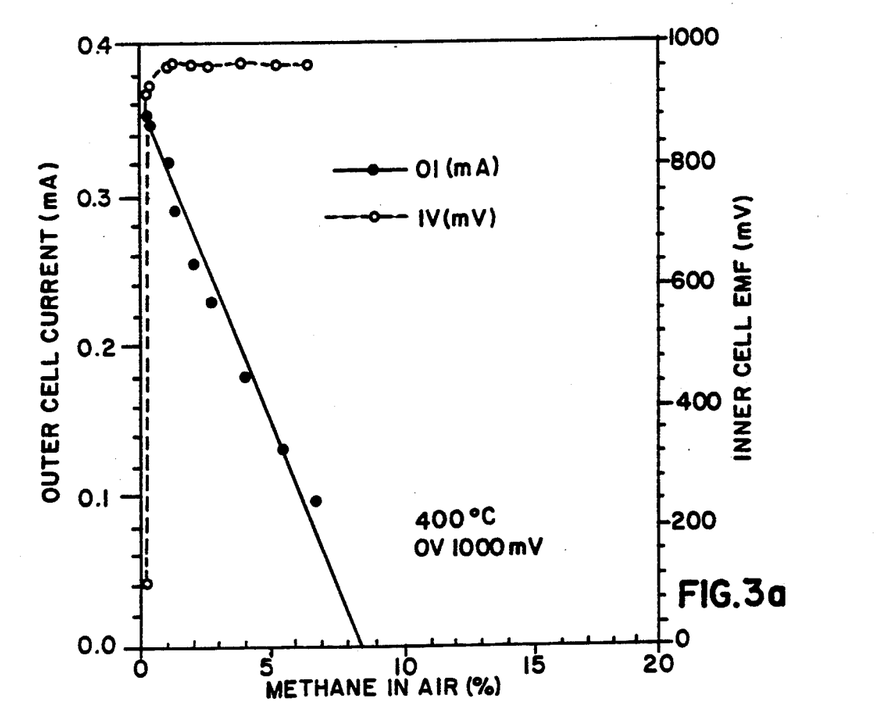
Figure 3B:
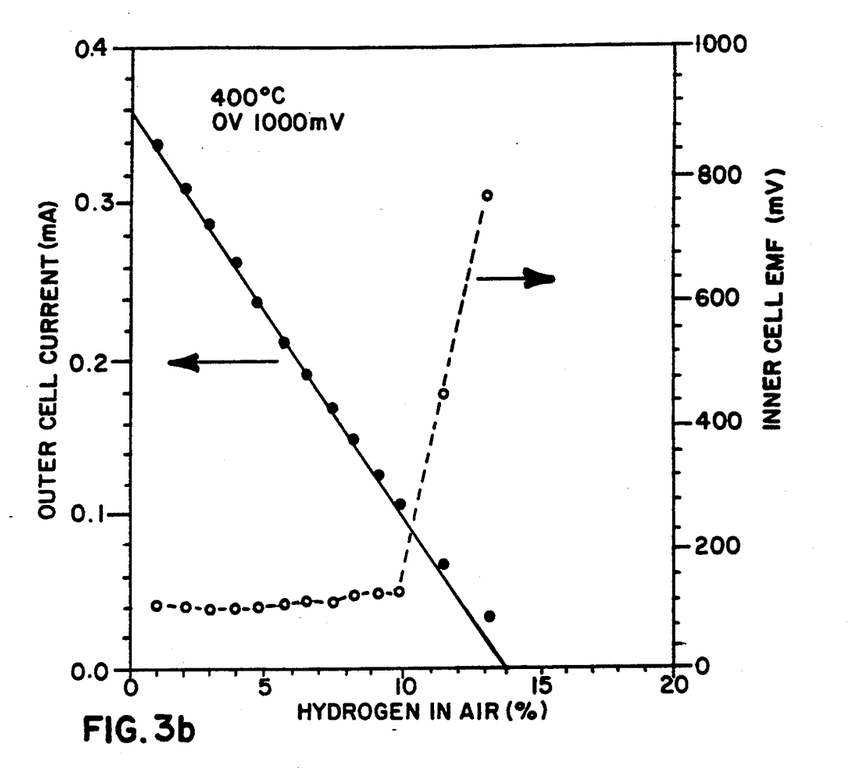

The level of the lower plateau depends upon the identity and concentration of the reactive gas in the test atmosphere, as seen in FIG. 3(a) and 3(b) for various mixtures of air/methane, and air/hydrogen.

The higher of the two plateaus occurs because at higher pumping voltages the catalytic reaction involving the gas is stopped electrochemically or the fully oxidized gas is electrochemically decomposed. The level of the higher plateau also depends on the identity and concentration of the reactive gas in the test atmosphere as seen in FIG. 2(a) and 2(b) for the gas mixtures of air/methane and air/hydrogen.

The reactive gas can be almost any gas, not necessarily limited to methane and hydrogen.

Figure 2C:
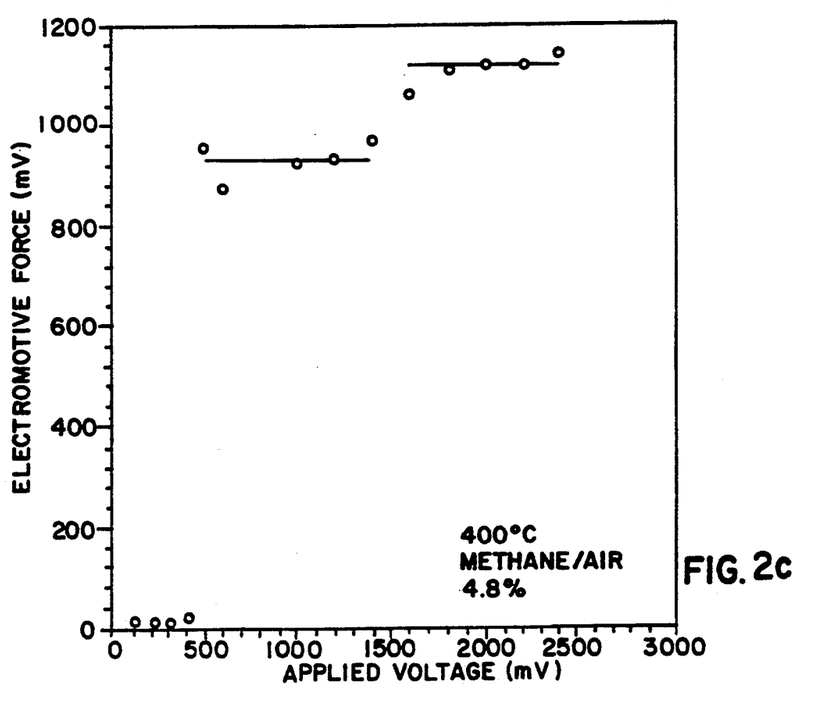

While the first and second electrodes are engaged in pumping oxygen electrochemically the third and fourth electrodes (211 and 212) can be utilized to measure an emf (Nernst voltage). Because of the electrochemical pumping action happening at electrodes 111 and 112, the oxygen activity in chambers 114 and 214 is different from that in ambient gas 104. Therefore based on the Nernst principle, an emf should be generated across the electrodes 211 and 212. Its magnitude can be divided into two components with each corresponding to the two pumping voltage ranges which generate the current plateaus across the electrodes 111 and 112. A typical result is shown in FIG. 2(c) for a air/methane gas mixture.

Figure 2D:
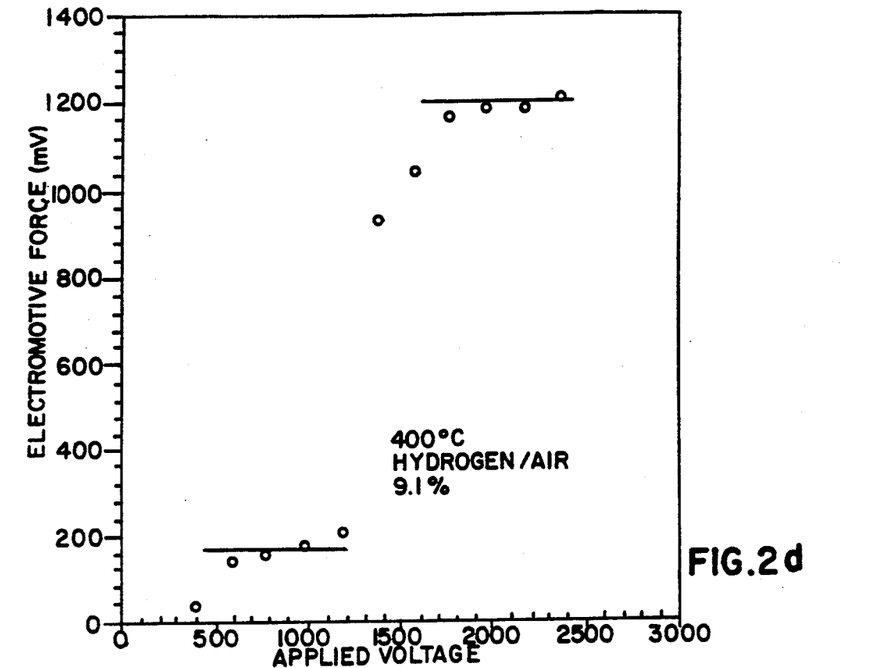

Different gases have different emf values. For a comparison, the emf generated by a gas mixture of air/hydrogen is given in FIG. 2(d). In FIG. 3(a) and 3(b), both the current (lower plateau) and corresponding emf readings (Nernst voltage) are given for various amounts of methane and hydrogen in air. The outer cell corresponds to chamber 114 and the inner cell corresponds to chamber 214.

As a common feature of all embodiments of the invention, the test atmosphere is tested at one pumping voltage and one emf reading. The lower pumping voltage is chosen to be of a magnitude for the oxygen limiting current to be on a lower plateau for the first pair electrodes. The magnitude of the current is measured. While the oxygen pumping is ongoing, an emf is measured from the second pair of electrodes. If all other parameters such as oxygen concentration and temperature are constant, the current level and the emf magnitude are determined by the identity and concentration of the unknown component. The converse is also true. Both the identity and concentration of the unknown component are deduced from the measured current and emf levels.

Figure 4:
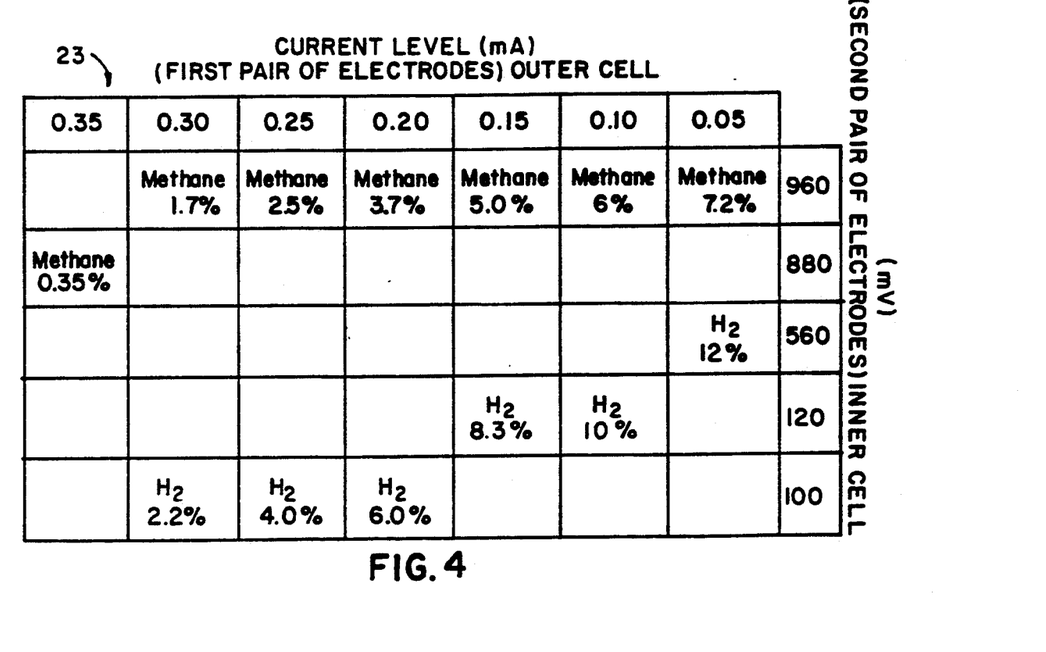
FIG. 4 is a table correlating gas identity and concentration with the limiting electric current and the emf values.

As another feature of the invention, there is provided a table containing pairs of numbers representing different combination of current and emf levels. As an example, a column may represent the value of a low current plateau, while a row may represent the value of an emf level. For each pair of current-emf levels, i.e. the intersection of a column and row, the table provides the identity and concentration of the corresponding gas component. Data are obtained from measurements of known concentrations of components, such as presented in FIG. 3(a) and 3(b). An abridged table 23 is illustrated by FIG. 4.

Figure 5:
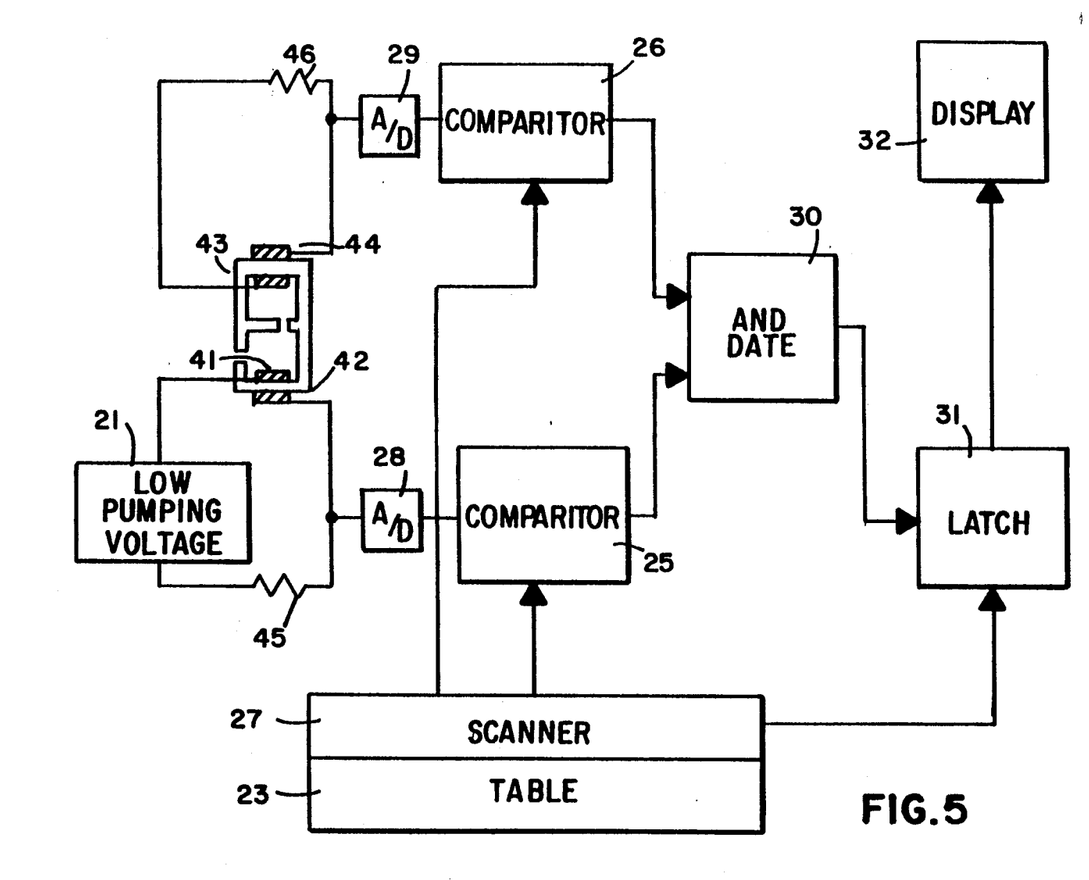
FIG. 5 is a block diagram of a first preferred embodiment of apparatus contemplated by the invention.

Shown in FIG. 5 is a preferred embodiment of the invention, the electrodes 41, 42 are coupled to a voltage source 21 which provides a voltage of a magnitude that causes the oxygen limiting current to be on a lower plateau. The electrodes 43, 44 are used for the emf measurement.

The current and the emf values are measured by reading the voltage across the two series resistors 45, 46. The obtained values are compared to pairs of numbers representing different combinations of current and emf which are contained in a look-up table 23 such as seen in FIG. 4. The best match between the measured current-emf pair and the tabulated pairs in table 23 determines the identity and concentration of the gas component in the gas mixture.

The current and emf are measured and digitized by A/D converters 28, 29. The digitized signals representing the current and emf are coupled to corresponding digital comparators 25, 26. The table 23 containing pairs of numbers is scanned. Table 23 may be digitally stored in ROM and accessed by scanner 27. A digital signal representing the current is directed to the digital comparator 25 coupled to the electrodes 41, 42, with the lower current plateau. A digital signal representing the emf is directed to the digital comparator 26 coupled to the electrodes 43, 44. As the table 23 is scanned, the stored numbers are compared to the measured current-emf values. The outputs of the two digital comparators 25, 26 are inputted to an AND-gate 30. When there is a match with both measured current values and emf values for a stored number pair both digital comparators 25 and 26 provide output signals which enables AND-gate 30, which closes a latch 31. Latch 31 is interposed between look-up table 23 and a display 32. When latch 31 is closed the component identity and concentration corresponding to the matched pair, and therefore the measured current-emf values, is read from the table 23 and indicated upon display 32. Analog comparators can be used instead of digital comparators if the A/D converters 28, 29 are eliminated and D/A converters are used at the outputs of table 23.

Figure 6:
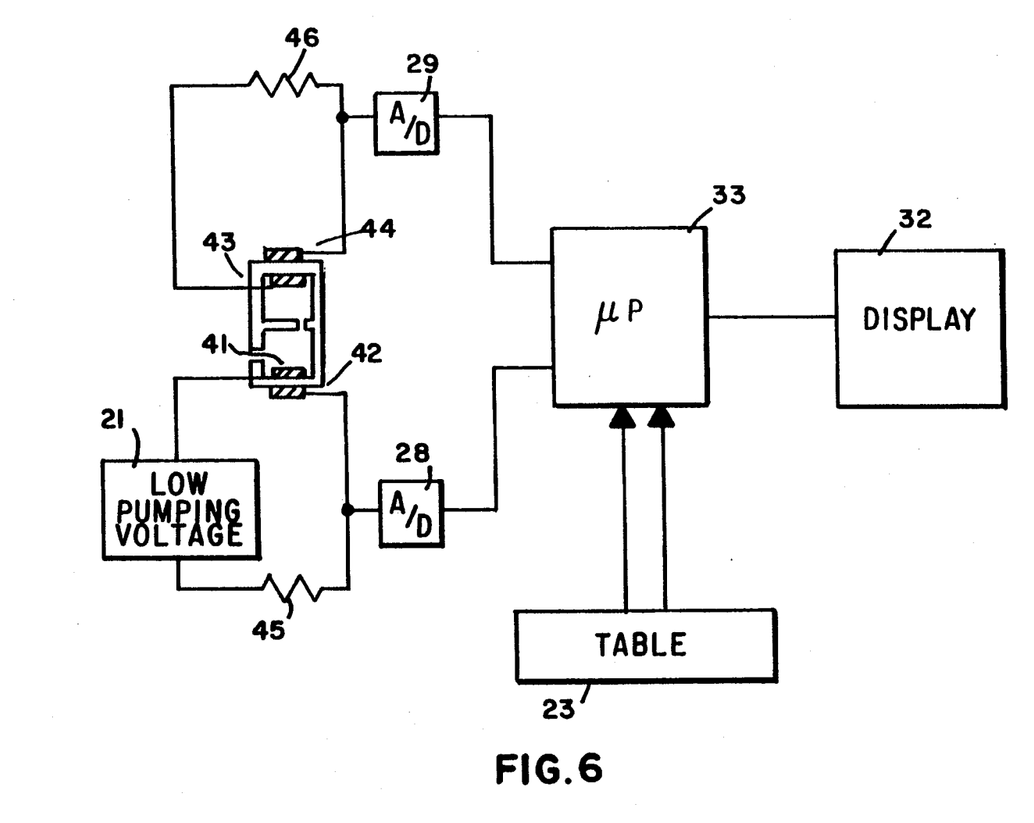
FIG. 6 shows apparatus similar to that of FIG. 5 in which the comparisons between measured and table values are made by a microprocessor.

In a variation of this embodiment, as shown in FIG. 6, the comparisons between measured and tabulated values may be made by a microprocessor 33.

For the gas mixture in which the stoichiometric ratio between the reactive gas and the oxygen is exceeded, (i.e., more reactive gas than oxygen) the apparatus of FIG. 1 can also be used to determine reducing gas concentration and identity. FIGS. 7 and 8 show the operation of the apparatus when the reducing gas is above the stoichiometric concentration when mixed with air. When a sufficient positive voltage is applied between the first and second electrodes 111, 112, oxygen is pumped from atmosphere 104 through the solid electrolyte wall 113 to the gaseous mediums 114 and 214. This pumping voltage is provided by pumping voltage source 116.

In response, electric current will flow through solid electrolyte wall 113 and is called the oxygen limiting current. The oxygen limiting current may be determined by measuring the voltage across a resistor 117 in series with the pumping voltage source 116 and the sensor. The physical barrier 118, such as a small aperture or a gas permeable membrane is provided between the chamber 114 and test atmosphere 104 for limiting the flow of reactive gas from the test atmosphere 104 to the first electrode 111 in such a way that for a wide range of pumping voltages the oxygen current is at limiting level, i.e., nearly constant as the pumping voltage is varied over a range.

Figure 7A:
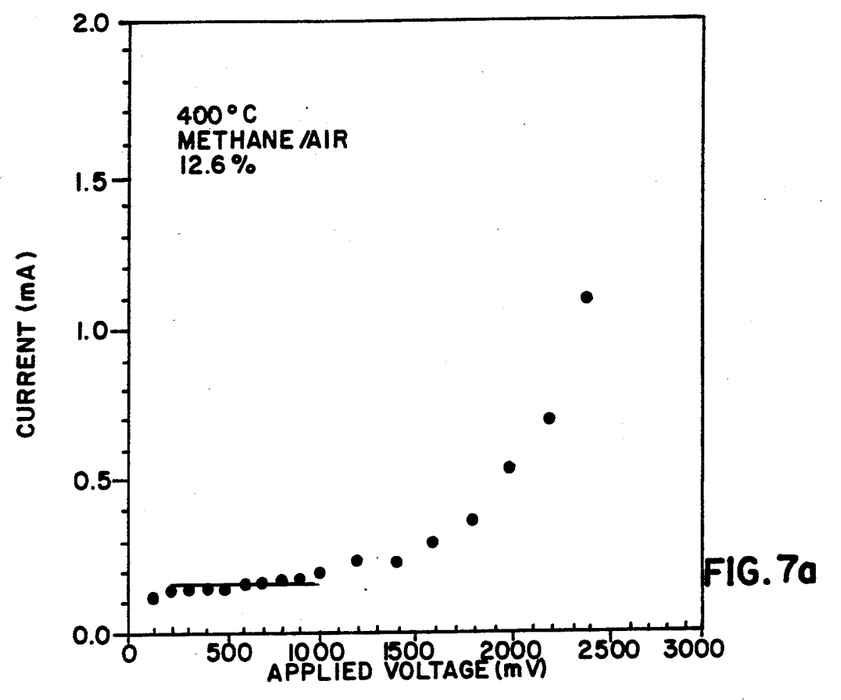
Figure 8A:
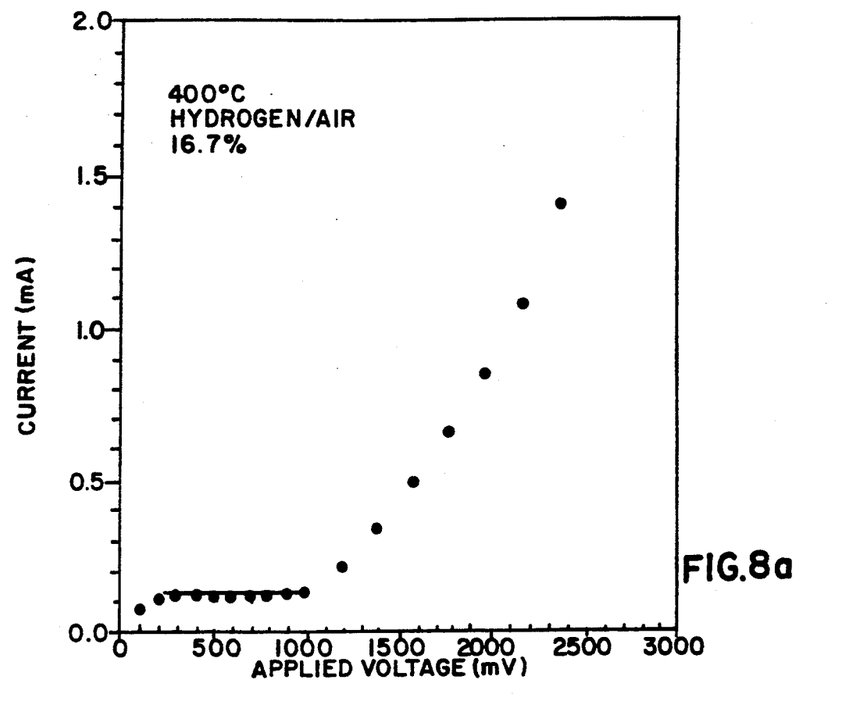

This phenomenon of current plateaus is illustrated by the curve in FIGS. 7(a) and 8(a) where a plateau occurs for a methane/air gas mixture and a hydrogen/air gas mixture. For both cases, the limiting current occurs for a pumping voltage between 100 mV and 1100 mV.

The plateaus shown in FIGS. 7(a) and 8(a) occur because at low positive pumping voltages (< 1100 mV), the gas mixture inside the chamber 114 wants to maintain a stoichiometric ratio condition, with the reactive gas exactly balanced by the oxygen. Since the flow of the reactive gas is limited by the gas aperture 118, the balancing oxygen which is supplied by the pumping has a limiting value. When the gas concentration is fixed, the value of the limiting oxygen current is proportional to the size of the aperture and inversely proportional to its length. When the shape of the gas aperture is fixed, the limiting oxygen current is proportional to the concentration of the reactive gas.

The magnitude of the plateau depends upon the identity and concentration of the reactive gas in the test atmosphere, as seen in FIGS. 7(a) and 8(a).

When the applied pumping voltage exceeds 1100 mV, the stoichiometric condition in chamber 114 is unbalanced by an excess amount of oxygen which is supplied by the pumping voltage (see FIGS. 7(a) and 8(a)).

The reactive gas can be almost any gas, not necessarily limited to methane and hydrogen.

Figure 7B:
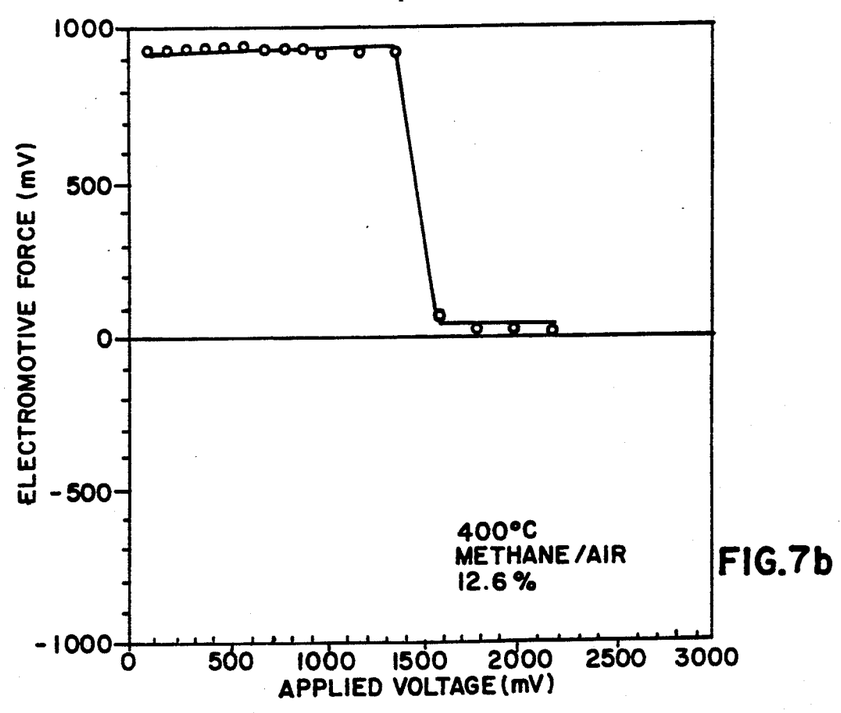
Figure 8B:
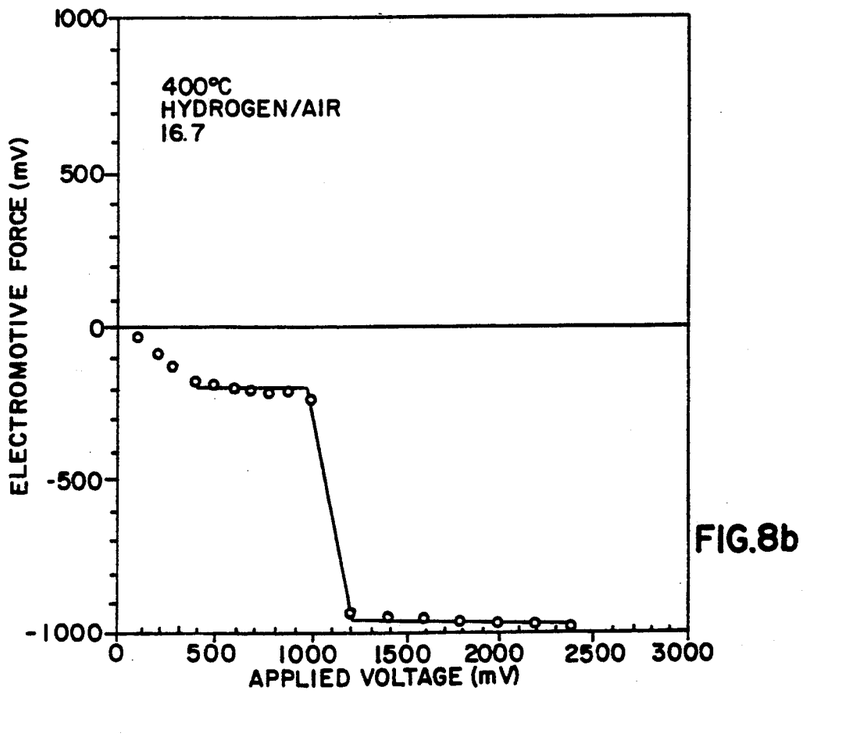

While the first and second electrodes are engaged in pumping oxygen electrochemically, the third and fourth electrodes (211 and 212) can be utilized to measure an emf (Nernst voltage). Because of the electrochemical pumping action occurring at electrodes 111, 112, the oxygen activities in chambers 114 and 214 are different from that in ambient gas 104. Therefore based on the Nernst principle, an emf is generated across electrodes 211 and 212. Its magnitude can be divided into two component with the pumping voltage 1100 mV as the dividing point. Typical results are shown in FIGS. 7(b) and 8(b) for gas mixtures of air/methane and air/hydrogen. As illustrated in both figures, different gases provide different emf magnitudes and polarities.

Figure 9:
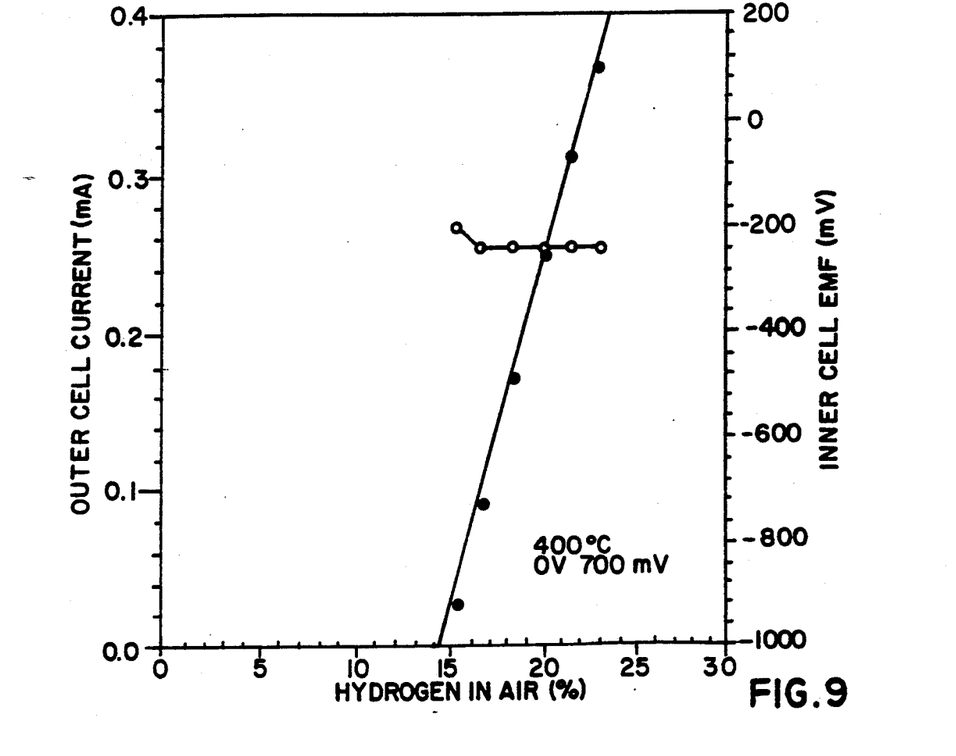
FIG. 9 shows the linear relationships between the plateau limiting current (dark circles) and the gas concentration for hydrogen gas mixtures. In the same plots, the corresponding emf readings (open circles) are given.

In FIG. 9, a plot of measured limiting current and emf values versus the hydrogen concentration in air is given. The important property of such sensor device is evident through the illustration of this figure. The measured lower level of the hydrogen concentration in air by this invention is lower than the stoichiometric concentration (14.5% vs 29.52%). This is because the diffusion constant of hydrogen in air is almost twice that of the oxygen in air, therefore the stoichiometry inside chamber 114 is achieved even though the hydrogen concentration of test gas 104 is only half of the theoretical value under the standard condition.

As a common feature of all embodiments of the invention, the test atmosphere is evaluated at one pumping voltage and one emf reading. The lower pumping voltage is chosen to be of a magnitude for the oxygen limiting current to be on a plateau for the first pair of electrodes. The magnitude of the current is measured. While the oxygen pumping is operating an emf is measured at the second pair of electrodes. If all other parameters such as oxygen and temperature are constant, the current level and the emf magnitude and its polarity are determined by the identity and concentration of the unknown component. The converse is also true. Both the identity and concentration of the unknown component in a known carrier gas are deduced from the measured current and emf magnitude and polarity.

Figure 10:
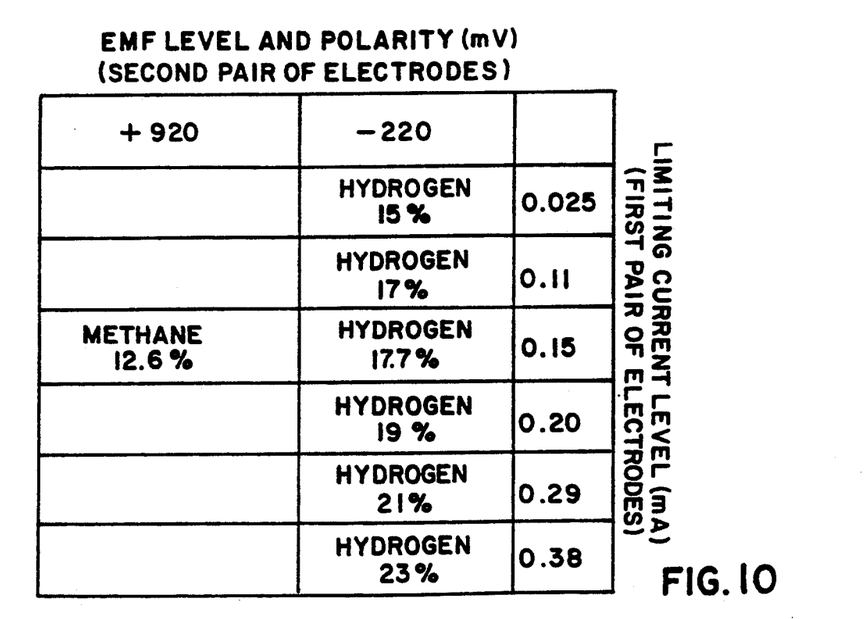
FIG. 10 is a table correlating gas identity and concentration with the limiting electric current and the emf value.

As another feature of the invention, there is provided a table containing pairs of numbers representing different combinations of current and emf levels. As an example, a column may represent the value of a low current plateau, while a row may represent the value of an emf level. For each pair of current-emf levels, i.e. the intersection of a column and row, the table provides the identity and concentration of the corresponding component (see FIG. 10). The data in the table are from measurements obtained from known concentrations of components, such as presented in FIGS. 8 and 9.

Shown in FIG. 5 is a preferred embodiment of the invention, the electrodes 41, 42 are coupled to a pumping voltage source 21 providing a negative voltage of a magnitude which causes the oxygen limiting current to be on a plateau. The electrodes 43, 44 are for the emf measurement.

The current and the emf readings are measured, e.g. by reading the voltage across corresponding series resistors 45, 46, and are compared to pairs of numbers representing different combinations of current and emf which are tabulated in a look-up table 23 which has been determined from experimental data. The best match is obtained between the measured current-emf and the tabulated pairs, and the corresponding component identity and concentration is read from the table.

The current and emf are measured and digitized by A/D converters 28, 29. The digitized signals representing the current and emf are coupled to corresponding digital comparators 25, 26. The tables 23 containing pairs of numbers is scanned. Table 23 may be stored digitally in ROM and accessed by scanner 27. A digital signal representing the current is directed to the digital comparator 25 coupled to the electrodes 41, 42 with the lower current plateau. A digital signal representing the emf is directed to the digital comparator 26 coupled to the electrodes 43, 44. As the table 23 is scanned, the stored numbers are compared to the measured current-emf values. The outputs of the two digital comparators 25, 26 are inputted to an AND-gate 30. When there is a match with both measured current values and a stored number pair both digital comparators 25 and 26 provide output signals which enables AND-gate 30, which in response closes a latch 31. Latch 31 is interposed between look-up table 23 and a display 32. When latch 31 is closed the component identity and concentration corresponding to the matched pair, and therefore the measured current-emf values, is read from the table 23 and indicated upon display 32. Analog comparators can be used instead of digital if the A/D converters 28, 29 are eliminated and D/A converters used at the outputs of table 23.

In a variation of this embodiment, as shown in FIG. 6, the comparisons between measured and table values may be made by a microprocessor 33.

Figure 11:
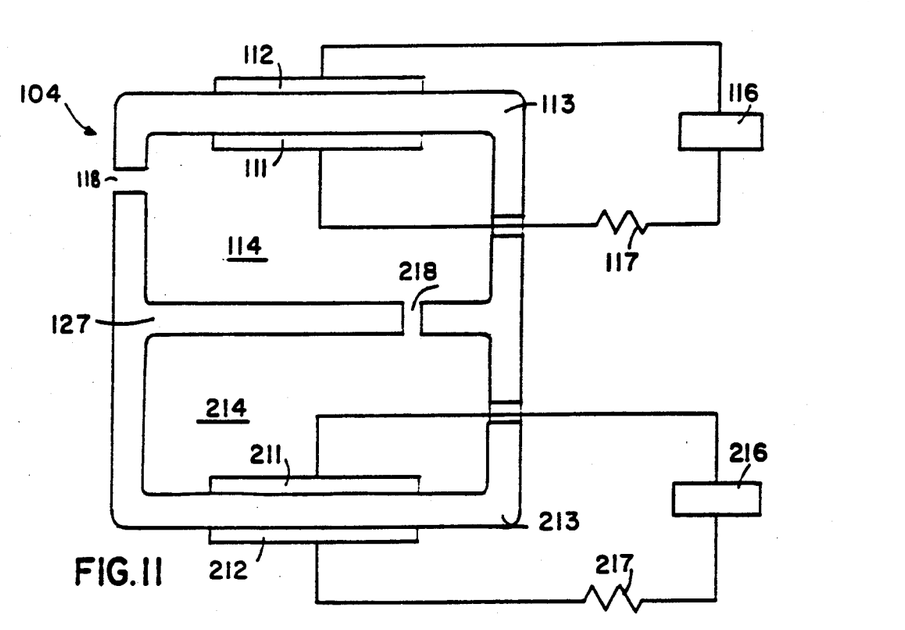
FIG. 11 illustrates, in schematic form, another multigas sensor suitable for practicing the invention.

In an alternate embodiment of the present invention, the pair of electrodes of the second solid electrolyte wall can be operated in an alternate mode. In this alternate mode the cell, which includes the pair of electrodes and the chamber operate as a oxygen pump or in a "pumping" mode. FIG. 11 illustrates, in schematic form, an oxygen sensor 200 suitable for practicing the invention. It has an identical construction as that of the sensor 100 illustrated in FIG. 1, except a power supply 216 and a resistor 217 are connected to electrodes 211 and 212.

To practice the method of the present invention, the test atmosphere should contain a known percentage of oxygen before mixing the gases and may be air with an unknown component such as a reactive gas. The purpose of the method is to determine the concentration of the known or unknown component. In the case where an unknown component is involved in the gas mixture, the determined concentration will be expressed as hydrogen-equivalent concentration which treats the unknown component as hydrogen gas. Once the identity of the unknown component is determined, its true concentration can be easily converted from the hydrogen-equivalent concentration back to the true concentration.

In the sensing operation, the whole sensor is immersed in the test atmosphere. When a sufficient negative voltage is applied between the first and second electrodes 111 and 112, oxygen is pumped from atmosphere 114 through the solid electrolyte wall 113 to the gaseous medium 104. In response, electric current will flow. As explained at the beginning of this section, the pumping current has two limiting or two "plateau" stages depending on the magnitude of the applied negative pumping voltage.

While the first and second electrodes are pumping the oxygen out of chamber 114, a second negative voltage is applied to the third and fourth electrodes, 211 and 212. The important property of such a sensing device is that the responding pumping current of the third and the fourth electrodes is linearly proportional to the concentration of the reactive gas.

Figure 12:
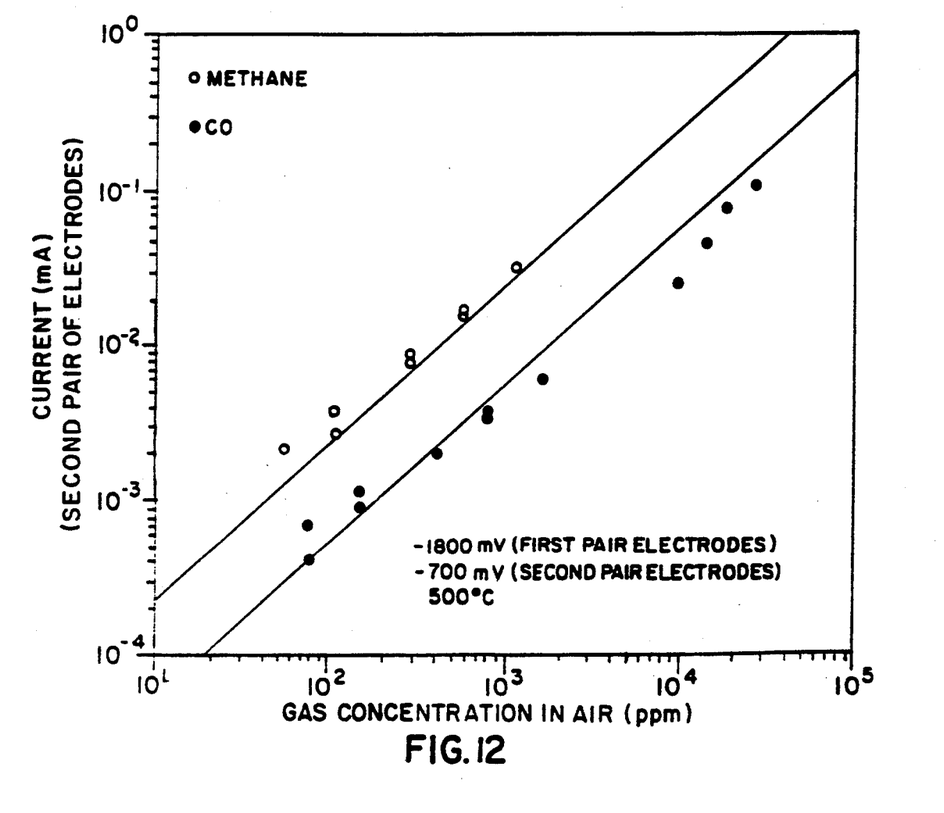
FIG. 12 shows a comparison of a methane/air mixture and a carbon-monoxide/air mixture when operating the device as described in FIG. 11.

A typical example is given in FIG. 12 in which a negative pumping voltage with a magnitude of 1800 mV is applied to the first and second electrodes and a second negative voltage with a magnitude of 700 mV is applied to the third and the fourth electrodes. The responding current of the third and fourth electrodes is plotted against the concentration of methane and carbon monoxide with air as the carrier gas. Note that the polarity of the electric current for both gas mixtures is opposite to the polarity of the applied voltage. This is because while the pumping current of the first and second electrodes is at its high plateau, the low oxygen activity within the chambers 114 and 214 will sustain a emf across the third and fourth electrodes with a value higher than 950 mV for most of the reactive gases (examples are given in FIGS. 2(c) and 2(d)). Applying a negative voltage to the third and fourth electrodes with a magnitude lower than 950 mV would then yield a current opposite to the polarity of the applied voltage. Also the ratio of the responding currents of the third and fourth electrodes for methane and CO gas mixtures is four. This is because methane needs four times as much oxygen as that of CO to be fully oxidized.

Figure 13:
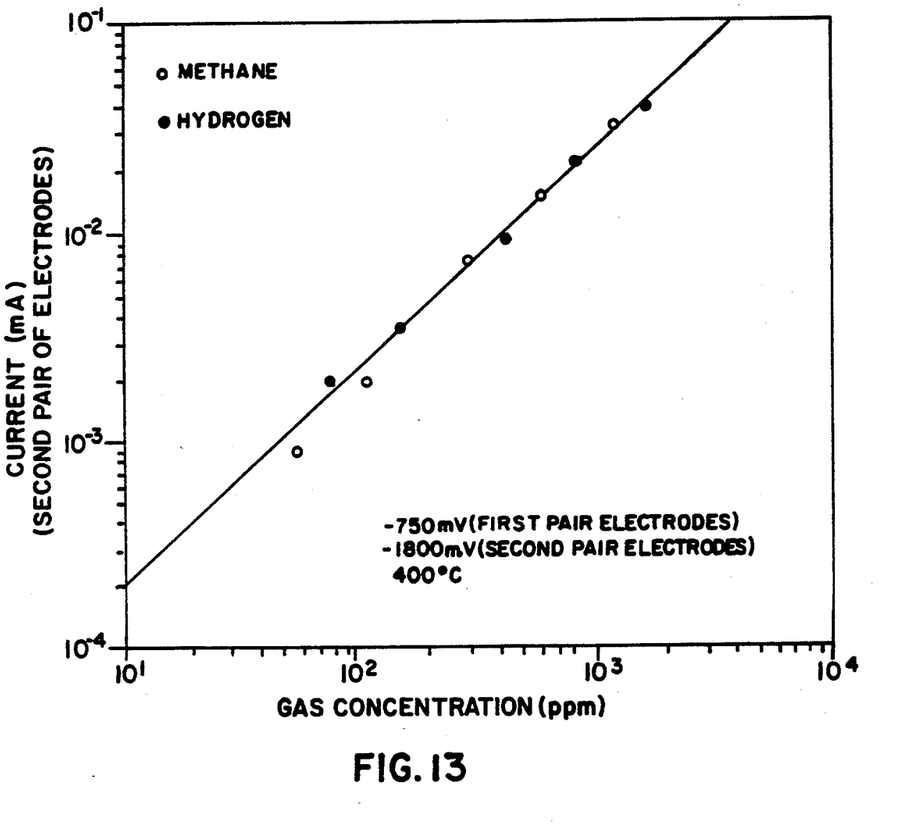
FIG. 13 shows a comparison of a methane/air mixture and a hydrogen/air mixture when operating the device as described in FIG. 11.

Another example is shown in FIG. 13 in which a negative pumping voltage with a magnitude of 750 mV is applied to the first and second electrodes and a second negative voltage with a magnitude of 1800 mV is applied to the third and fourth electrodes. The responding current is plotted against the concentration of methane and hydrogen in air. The linearity is observed between the electric current and the gas concentration but there is no difference in the current level between the two different gases. Also the current polarity is the same as that of the applied voltage. This is because the applied voltage is larger than the level of the emf generated at the second pair of electrodes.

As a common feature of the invention, the test atmosphere is measured at two pumping voltages. A negative voltage is applied to the first and second electrodes 111, 112 with a magnitude such that the corresponding pumping current is in its high (or low) plateau level. At the same time a second negative pumping voltage is applied to the third and fourth electrodes 211, 212 with a magnitude which would cause the pumping current of the first and second electrodes in its low (or high) plateau level if applied to the first and second electrodes. In the case when a low magnitude of pumping voltage is applied to the third and fourth electrodes as the second negative pumping voltage, its magnitude is preferably less than 950 mV. The magnitude of the responding current generated between the third and fourth electrodes is measured. The concentration of the test gas is deduced from the measured current levels. A convenient way is using calibration data such as those presented in FIGS. 12 and 13 to determine the concentration or the hydrogen-equivalent concentration of the test gas.

The present invention has been described in detail, including the preferred embodiments thereof. However, it will be appreciated by those skilled in the art upon consideration of the present disclosure, that various alterations and modifications may be made that are within the scope and spirit of the invention as set forth in the appended claims.

What is claimed is:

1. A method for determining the identity and concentration of a component in a test atmosphere having a known concentration of oxygen comprising:
   providing a solid electrolyte oxygen sensor having a first solid electrolyte wall in contact with an interposed between a first electrode and a second electrode and a second solid electrolyte wall in contact with an interposed between, a third and a fourth electrode, said second and fourth electrode in communication with said test atmosphere, a partition wall interposed between said first and third electrodes which creates a first chamber and a second chamber, said sensor having a first gas-flow limiting means between the test atmosphere and the first chamber and a second gas-flow limiting means between the first chamber and the second chamber;
   applying a first negative voltage across said first and second electrodes, causing electrochemical oxygen pumping and a first electric current to flow through the first electrolyte wall, said first negative voltage of a magnitude to cause said first electric current to be on a first current limiting plateau;
   measuring the magnitude of said first electric current;
   measuring the magnitude of an open cell EMF across said third and fourth electrodes;
   providing a table correlating pairs of numbers representing various combinations of first electric currents and open cell EMF's with corresponding identity and concentration of one or more components; and
   matching the measured magnitudes of said first electric current and open cell EMF with said pairs of numbers in said table and determining the corresponding identity and concentration of one or more component.

2. The method of claim 1 wherein said first and second electrolyte wall is made of yttria or calcia stabilized zirconia.

3. A method for determining the identity and concentration of a component in a test atmosphere having a known concentration of oxygen wherein the concentration of the component is larger than that of a stoichiometric gas mixture comprising:
   providing a solid electrolyte oxygen sensor having a first solid electrolyte wall in contact with and interposed between a first electrode and a second electrode and a second solid electrolyte wall in contact with and interposed between, a third and a fourth electrode, said second and fourth electrode in communication with said test atmosphere, a partition wall interposed between said first and third electrodes which creates a first chamber and a second chamber, said sensor having a first gas-flow limiting means between the test atmosphere and the first chamber and a second gas-flow limiting means between the first chamber and the second chamber;

applying a first positive voltage across said first and second electrodes, causing electrochemical oxygen pumping and a first electric current to flow through the first electrolyte wall, said first positive voltage of a magnitude to cause said first electric current to be on a current limiting plateau;

measuring the magnitude of said first electric current;

measuring the magnitude of an open cell EMF across said third and fourth electrodes;

providing a table correlating pairs of numbers representing various combinations of first electric currents and open cell EMF's with corresponding identity and concentration of one or more components; and matching the measured magnitudes of said first electric current and said open cell EMF with said pairs of numbers in said table and determining the corresponding identity and concentration of one or more component.

4. The method of claim 3 wherein said first and second electrolyte wall is made of yttria or calcia stabilized zirconia.

5. A method for determining the concentration of a known component or hydrogen-equivalent concentration of an unknown component in a test atmosphere having a known concentration of oxygen comprising:

providing a solid electrolyte oxygen sensor having a first solid electrolyte wall in contact with and interposed between a first electrode and a second electrode and a second solid electrolyte wall in contact with and interposed between, a third and a fourth electrode, said second and fourth electrode in communication with said test atmosphere, a partition wall interposed between said first and third electrodes which creates a first chamber and a second chamber, said sensor having a first gas-flow limiting means between the test atmosphere and the first chamber and a second gas-flow limiting means between the first chamber and the second chamber;

applying a first negative voltage across said first and second electrodes, causing electrochemical oxygen pumping and a first electric current to flow through the first electrolyte wall, said first negative voltage of a magnitude to cause said first electric current to be on a first current limiting plateau;

measuring the magnitude of said first electric current;

applying a second negative voltage across said third and fourth electrodes causing electrochemical oxygen pumping and a second electric current to flow through the corresponding second electrolyte wall, said second negative voltage of a magnitude to cause said first electric current to be on a second current plateau;

measuring the magnitude of said second electric current;

providing a table correlating numbers representing second electric currents with corresponding concentration of the known component or hydrogen-equivalent concentration of the unknown component;

matching the measured magnitude of second electric current with said numbers in said table and determining the corresponding concentration of the known component or hydrogen-equivalent of the unknown component.

6. The method of claim 5 wherein said first and second electrolyte wall is made of yttria or calcia stabilized zirconia.

* * * * *